(12) United States Patent
Kanai et al.

(10) Patent No.: US 6,367,502 B1
(45) Date of Patent: Apr. 9, 2002

(54) FLOW CONTROL DEVICE

(75) Inventors: Masahiro Kanai, Tokyo; Etsumi Nagaya, Koshigaya, both of (JP)

(73) Assignee: Aubex Corporation, Tokyo (JP)

( * ) Notice: Subject to any disclaimer, the term of this patent is extended or adjusted under 35 U.S.C. 154(b) by 0 days.

(21) Appl. No.: 09/666,182

(22) Filed: Sep. 21, 2000

(30) Foreign Application Priority Data

Sep. 22, 1999 (JP) ............................................ 11-268566

(51) Int. Cl.⁷ ............................................... F16K 35/00
(52) U.S. Cl. ....................... 137/556; 137/862; 137/383; 251/7
(58) Field of Search ...................... 251/4, 7; 137/383, 137/556, 862

(56) References Cited

U.S. PATENT DOCUMENTS

| 1,427,455 A | * | 8/1922 | Gates ............................. 251/7 |
| 3,316,935 A | * | 5/1967 | Kaiser et al. .................. 251/4 |
| 3,550,619 A | * | 12/1970 | Halasz ........................... 251/7 |
| 3,587,635 A | * | 6/1971 | Raymond ..................... 137/556 |
| 4,439,179 A |   | 3/1984 | Lueders et al. ................ 604/34 |
| 5,113,906 A | * | 5/1992 | Hogner ........................... 251/4 |
| 5,313,975 A | * | 5/1994 | Nimberger .................. 137/383 |
| 5,318,515 A |   | 6/1994 | Wilk ............................. 604/30 |
| 5,453,098 A |   | 9/1995 | Botts et al. .................. 604/250 |
| 5,718,409 A | * | 2/1998 | Starchevich .................... 251/4 |
| 5,853,398 A |   | 12/1998 | Lal et al. .................... 604/250 |

FOREIGN PATENT DOCUMENTS

| JP | 51-21927 | 2/1976 |
| JP | 5-84310 | 4/1993 |
| JP | Ep 0 722 745 | 7/1996 |

* cited by examiner

Primary Examiner—A. Michael Chambers
(74) Attorney, Agent, or Firm—Lowe Hauptman Gilman & Berner, LLP

(57) ABSTRACT

A flow control device has a body (41), a plurality of elastic flow control tube (51–54) provided in the body (41), a single fluid path (55) in communication with the flow control tube (51–54), a slider (56) slidable relative to the body (41), and a valve mechanism (71) for selectively pressing and shutting the flow control tube (51–54) in accordance with a slide position of the slider (56).

13 Claims, 12 Drawing Sheets

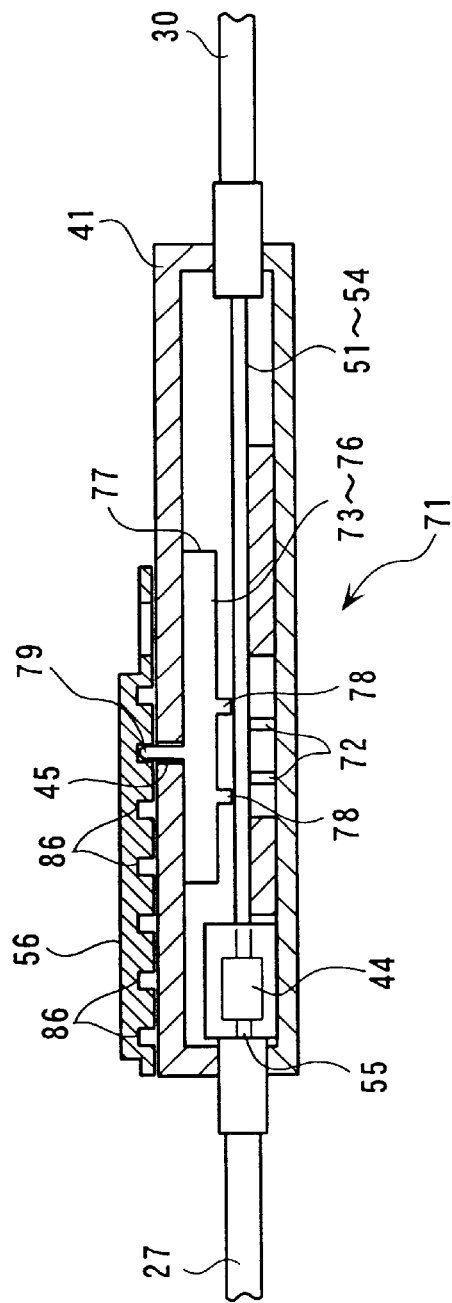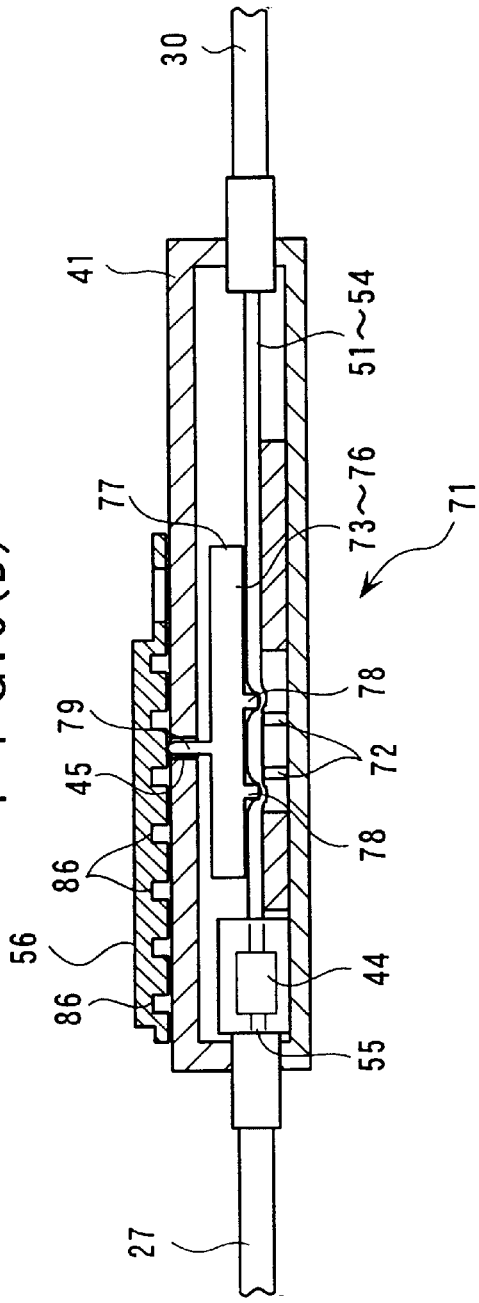

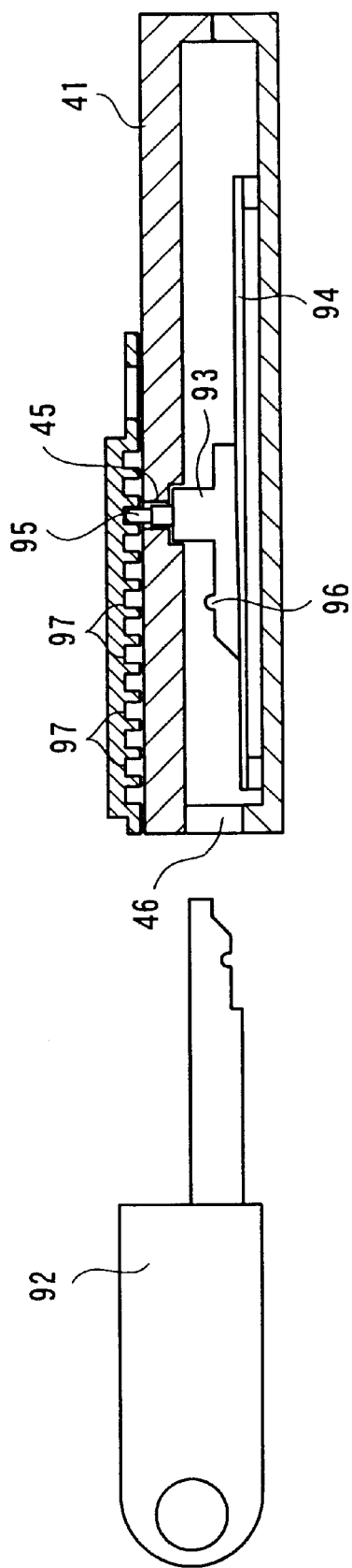
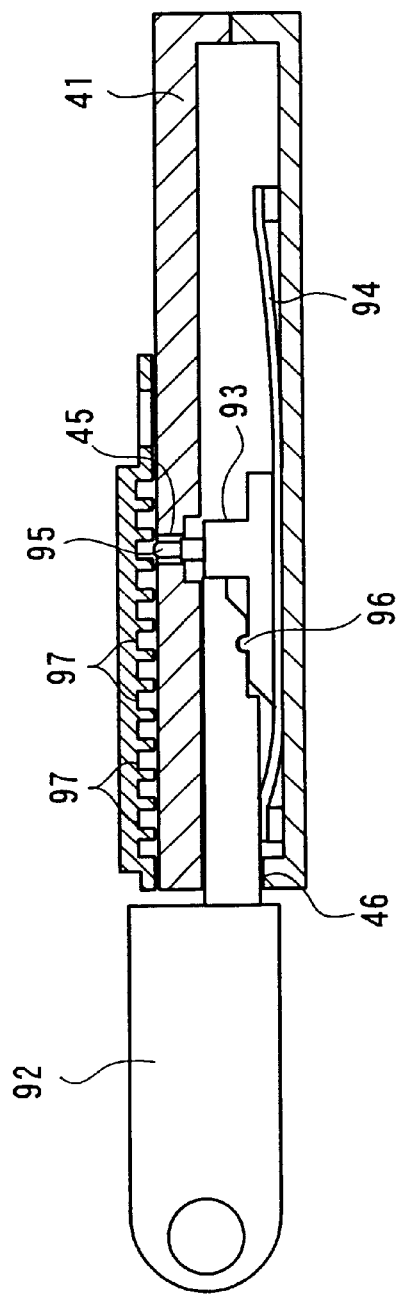
FIG. 10(A)
FIG. 10(B)

FLOW CONTROL DEVICE

BACKGROUND OF THE INVENTION

1. Field of the Invention

The present invention relates to a flow control device capable of switching supply of fluid flow, mainly liquid. More specifically, it relates to a flow control device capable of accurately controlling flow with a simple arrangement.

2. Description of Related Art

A liquid medicine injection apparatus, for instance, uses a tube with small diameter having conduit function and flow rate control function and the liquid medicine is supplied to the tube so that it is continuously injected into human body little by little.

Conventionally, flow rate of the liquid medicine injection apparatus having the conduit function and the flow rate control function is changed by exchanging the tube, which makes it impossible to change the flow rate immediately.

On the other hand, a device disclosed in Japanese Patent Application Laid-Open Publication No. Hei 5-84310 is known as a flow control device adapted for continuously injecting small amount of liquid medicine and capable of adjusting flow rate in a multistage.

The above device has a body including a cylindrical hollow valve chest in communication with the outside through an inflow hole and at least three outflow hole, and a plug body including a cylindrical valve portion rotatably accommodated in the valve chest, the valve portion provided with a slit opened in fan-shape and a straight-tube thin hole extending from a base portion of the slit to the radially opposite side, the fan-shaped slit being connected to the inflow hole when the thin hole is connected to either one of the outflow holes.

However, in the conventional arrangement, since the flow is switched by bringing the thin hole coincident with the either one of the outflow holes, when there is a gap between the thin hole and the outflow hole, the fluid can leak therefrom. Accordingly, inner diameter of the valve chest and the outer diameter of the valve portion have to be strictly sized, thus requiring processing accuracy and much production cost.

A seal member may be interposed between the thin hole and the outflow hole to alleviate the problem. However, rotation resistance of the valve portion can be increased, so that the rotation of the valve body can be deteriorated, thus making it difficult to control the flow rate easily and accurately.

SUMMARY OF THE INVENTION

An object of the present invention is to provide a flow control device being capable of overcoming the above-described conventional disadvantage, having a simple structure and being produced by a simple process, and being capable of easily and accurately controlling the flow rate.

The present invention is a flow control device, having a body, a plurality of elastic flow control tube provided inside the body, a slide member slidable relative to the body, and a valve mechanism for selectively pressing and shutting the flow control tube in accordance with a slide position of the slide member.

According to the above arrangement, when the slide member is slid, the plurality of flow control tube is selectively pressed and shut in accordance with the slide position of the slide member. As a result, the fluid is supplied through a flow control tube that is not pressed and shut, so that the flow rate can be controlled by selecting the flow control tube to be pressed and shut.

In this case, since the flow rate can be controlled only by selectively pressing and shutting the plurality of flow control tubes, the flow rate can be easily and accurately controlled as well as simplifying production process and structure thereof.

In the present invention, the valve mechanism may preferably include a stationary-side projection provided to the body to receive the respective flow control tubes, a plurality of press-piece provided in the body correspondingly to the respective flow control tube and displaceable in a direction to press the flow control tube toward the stationary-side projection, the plurality of press-piece having a movable-side projection at a position opposite to the stationary-side projection sandwiching the flow control tube and shifted longitudinally along the flow control tube relative to the stationary-side projection, and a cam provided to the slide member for selectively displacing the plurality of press-piece in accordance with the slide position of the slide member to press and shut a corresponding flow control tube.

According to the above arrangement, since the stationary-side projection provided to the body and the movable-side projection provided to the press-piece are shifted longitudinally along the flow control tube, when the press-piece is displaced by the cam to press the flow control tube, the flow control tube is shut by being sandwiched by the stationary-side projection and the movable-side projection in a shearing manner, so that the flow control tube can be securely pressed and shut with smaller force as compared to an arrangement where the stationary-side projection and the movable-side projection sandwich the flow control tube therebetween with the stationary-side projection and the movable-side projection located at corresponding position. Therefore, the flow rate can be more precisely controlled.

In the present invention, the stationary-side projection may preferably be provided at two longitudinally spaced locations along the flow control tube, and the movable-side projection may preferably be provided at two locations outside a position corresponding to the two stationary-side projections.

According to the above arrangement, since the press-piece presses the flow control tube with the two movable-side projections longitudinally spaced along the flow control tube, the press-piece can be displaced in a parallel attitude without being tilted. In other words, since the flow control tube is pressed and shut by the two stationary-side projections and the movable-side projections longitudinally spaced along the flow control tube, the flow control tube can be selectively pressed and shut more securely.

In the present invention, a positioning mechanism for locating the slide member at a position for the slide member to selectively press and shut the flow control tube may preferably be provided between the body and the slide member.

According to the above arrangement, since the slide member can be located at a position for selectively pressing and shutting the flow control tube, in other words, since the slide member can be retained at an adjusted position, adjusted flow rate can be stably continued.

In the present invention, a flow rate indication index may preferably be provided on the slide member, and a flow rate display may preferably be provided on the body for displaying a flow rate on a position corresponding to the flow rate indication index at respective positions of the slide member located by the positioning mechanism.

According to the above arrangement, since the current flow rate can be recognized by reading the flow rate shown on the flow rate display coinciding with the flow rate indication index provided on the slide member at the respective position located by the positioning mechanism, the adjustment can be simply and easily conducted.

In the present invention, the flow control device may preferably have a lock mechanism including a lock key capable of being inserted into and drawn off from the body, the lock key being drawn off from the body to lock a slide movement of the slide member, and the lock key being inserted to the body to allow the slide movement of the slide member.

According to the above arrangement, after the lock key is inserted to control the flow rate by sliding the slide member, the slide movement of the slide member can be locked by drawing off the lock key.

Accordingly, when the present invention is applied to, for instance, a liquid medicine injection apparatus for continuously injecting liquid medicine by a small amount, the lock key can be inserted by a doctor or a nurse to control the flow rate by sliding the slide member and the lock key can be drawn off, so that the security can be ensured since a patient cannot control the flow rate himself.

BRIEF DESCRIPTION OF THE DRAWINGS

FIG. 8 is a cross-section showing a flow control device used in the apparatus of the aforesaid embodiment;

FIGS. 10(A) and 10(B) are cross-sections showing a lock mechanism of a flow control device used in the apparatus of the aforesaid embodiment;

DETAILED DESCRIPTION OF PREFERRED EMBODIMENT(S)

A preferred embodiment of the present invention will be described below with reference to drawings.

Figure 1:
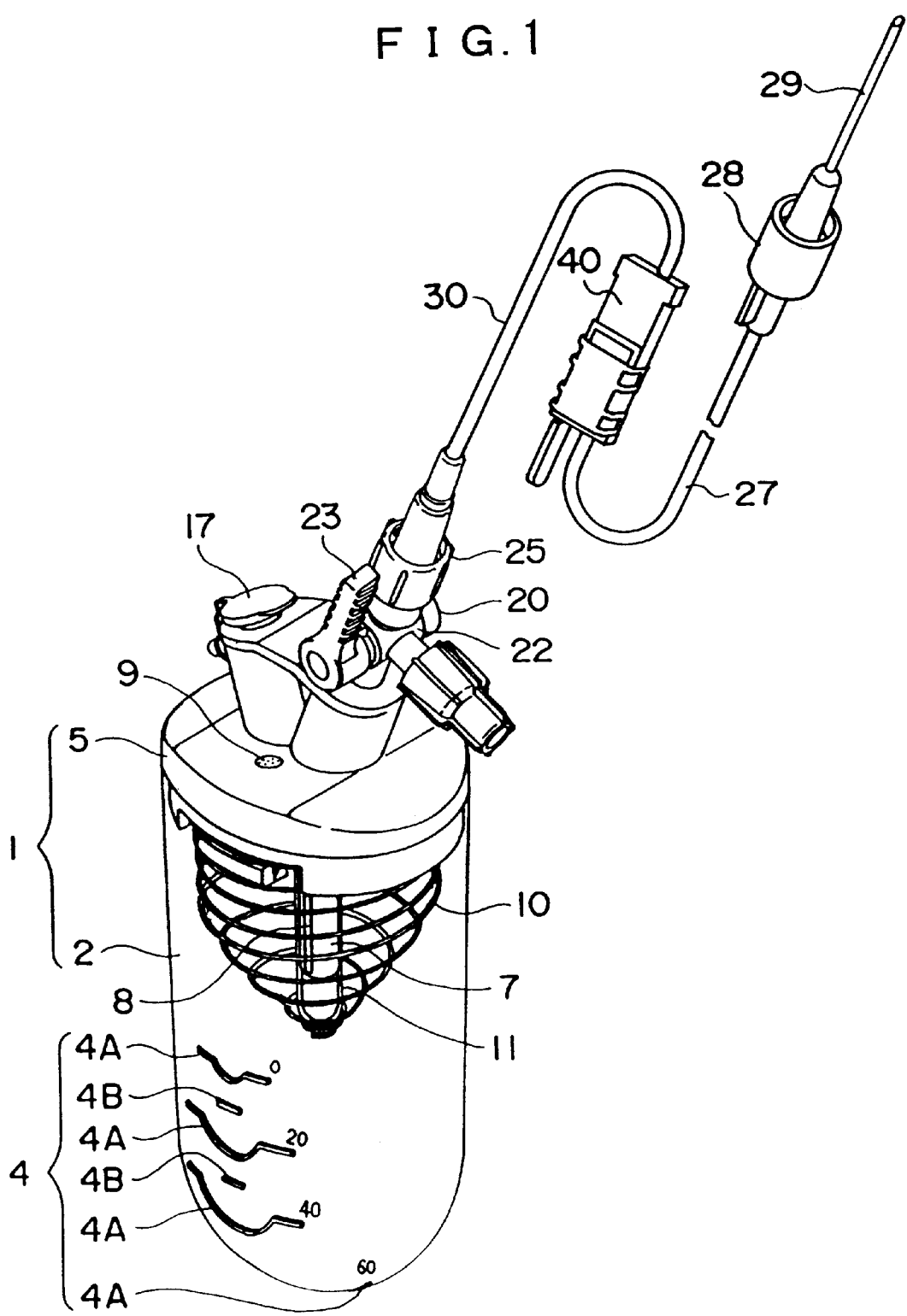
FIG. 1 is a perspective view showing a preferred embodiment of a fluid supplying apparatus embodying a flow control device according to the present invention.
Figure 2:
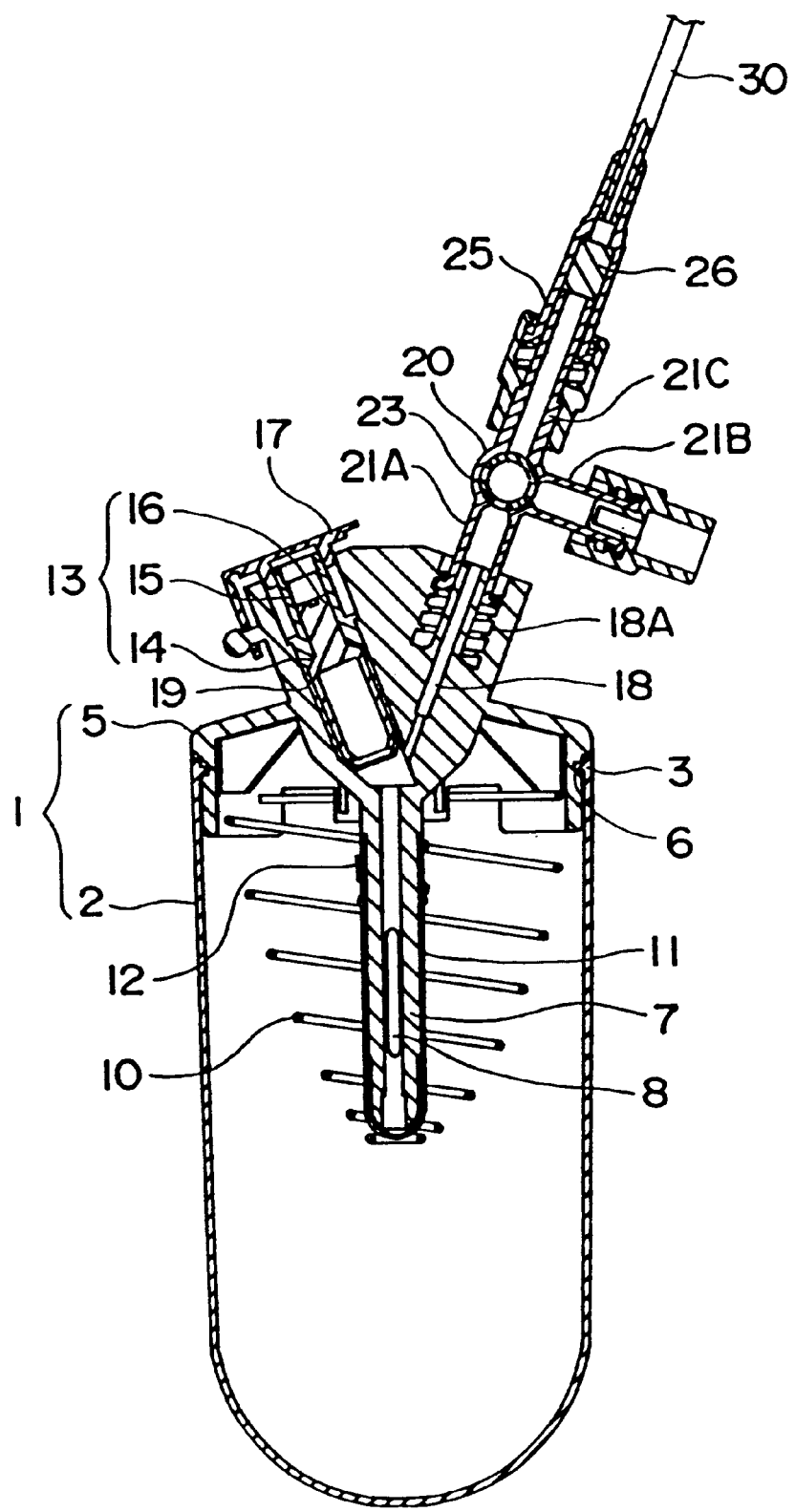
FIG. 2 is a cross-section of the aforesaid embodiment.

In the present embodiment, the present invention is applied to a liquid medicine injection apparatus for injecting liquid medicine to human body. FIG. 1 is a perspective view thereof, and FIG. 2 is a cross-sectional view thereof.

In the figures, a protection case 1 is composed of a bottomed cylindrical body 2 of transparent material such as plastic and glass, a lid body 5 made of polypropylene and fitted to an open end of the cylindrical body 2.

Figure 3:
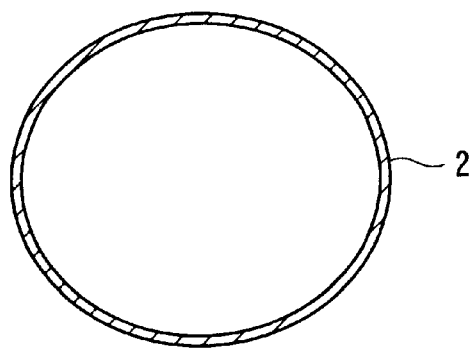
FIG. 3 is a cross-section of a protection case of the aforesaid embodiment.

The cylindrical body 2 is formed in a bottomed cylinder having an inner configuration of deformed cross-section except for circle, an oval here (see FIG. 3), and is provided with a projection 3 on inner side adjacent to the open end and a scale 4 on outer side, respectively. The scale 4 indicates liquid medicine containing amount (liquid medicine containing amount inside below-mentioned rubber elastic film 11) by cc unit from intermediate position in the up and down direction toward bottom. The scale 4 is composed of even number scale 4A of "0", "20", "40" and "60" and odd number scale 4B of "10", "30" and "50".

Figure 4:
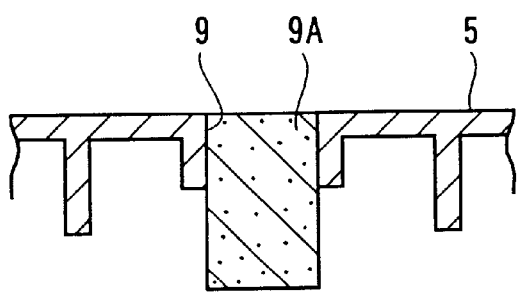
FIG. 4 is a cross-section of a water-repellant breathable filter of the aforesaid embodiment.

The lid body 5 has an engaging concave portion 6 for engaging the projection 3 of the cylindrical body 2 at an outer side thereof, an air vent 9 and a liquid medicine introduction tube 7 as a thin fluid introduction tube extending toward inside of the cylindrical body 2 substantially at the center of an upper side thereof. Both ends of the liquid medicine introduction tube 7 are opened and a plurality of slits 8 is provided on circumference thereof as shown in FIG. 4. The air vent 9 has a water-repellant breathable filter 9A for circulating air inside and outside of the protection case 1 and preventing the liquid medicine from permeating. A chemical-resistant synthetic resin bundle with water-repellant processing is preferably used as the water-repellant breathable filter 9A, for instance.

A rubber elastic film 11 with bottomed-tube shape is fitted in close contact with the liquid medicine introduction tube 7, an open end of the rubber elastic film 11 being held by a pinch 12. An outer diameter and length of the liquid medicine introduction tube 7 is substantially the same as an inner diameter and length of the contracted rubber elastic film 11. A maximum of 60 cc liquid medicine can be contained in the rubber elastic film 11. Incidentally, ordinarily approximate 20 cc liquid medicine is injected for cancer pain treating per one day, so that liquid medicine for approximately three days can be contained therein.

The rubber elastic film 11 is expanded in accordance with injecting and receiving the liquid medicine. A spring 10 stretching in proportion to the expansion of the rubber elastic film 11 is disposed at outer side thereof. The spring 10 is made of wire material having diameter of 0.6 mm to 0.8 mm, for instance. The spring 10 has an upper end stopped to the lid body 5 and is wound in a spiral manner so that the diameter thereof is gradually narrowed downward. The lowermost end is abutted to a pointed end of the liquid medicine introduction tube 7 through the rubber elastic film 11.

The rubber elastic film 11 is preferably made of a chemical-resistant material undamaged by a function of liquid medicine and having great toughness and stretchability, and transparent or translucent material is especially preferable. For example, silicone rubber and latex rubber on the market are preferable. The thickness of the rubber elastic film is approximately 0.4 mm. A contraction power when the liquid medicine is introduced in the rubber elastic film 11 is preferably 1000 to 7000 mmAq (millimeter by water head) pressure. Since venous pressure of human body is ordinarily around 60 mmAq, the liquid medicine can be introduced to a patient by a pressure more than 60 mmAq. When the contraction power of the rubber elastic film 11 falls below 1000 mmAq, it is difficult to be controlled. When the contraction power exceeds 7000 mmAq, the liquid medicine is difficult to be injected from the syringe into the rubber elastic film 11 by human power. However, the contraction power is not limited to the range described above.

An inflow hole 19 as a fluid inflow hole for injecting the liquid medicine into the rubber elastic film 11 and an outflow hole 18 as fluid outflow hole for discharging the liquid medicine received inside the rubber elastic film 11 are provided adjacently in V-shape on an upper portion of the liquid medicine introduction tube 7 (lid body 5). In other words, the inflow hole 19, the outflow hole 18 and the liquid medicine introduction tube 7 are provided to the lid body 5 in substantially Y-shaped arrangement and mutually in communication. A check valve 13 for allowing the inflow to the liquid medicine introduction tube 7 from the outside and preventing the outflow from the liquid medicine introduction tube 7 toward outside is provided inside the inflow hole 19. The check valve 13 has a valve cylinder 15 buried in the inflow hole 19 and having a valve seat 14 at the halfway thereof, and a chemical-resistant valve bar 16 made of silicone rubber and the like and retractably accommodated in the valve cylinder 15 to open and close the valve seat 14. Incidentally, a cap 17 can be detachably attached to an outer end of the valve cylinder 15. A spiral groove 18A for detachably engaging a three-direction valve 20 is formed around the outflow hole 18. The three-direction valve 20 has a valve body 22 with three switch holes 21A, 21B and 21C, and a cock 23 for switching the flow path.

A connector 25 provided on one end of a fluid delivering tube 30 having conduit function and flow rate control function is detachably connected to the switching hole 21C of the three-direction valve 20. A filter 26 for removing dust etc. in the liquid medicine is accommodated inside the connector 25. A flow control device 40 as a flow path selecting means is connected to the other end of the tube 30 and a connector 28 similar to the connector 25 is connected to the flow control device 40 through a tube 27 having therein a single flow path. A syringe needle 29 is detachably attached to a distal end of the connector 28 as an attachment to human body. Accordingly, the inside of the rubber elastic film 11 and the syringe needle 29 are connected through the fluid delivering tube 30, flow control device 40 and the tube 27.

Figure 5:
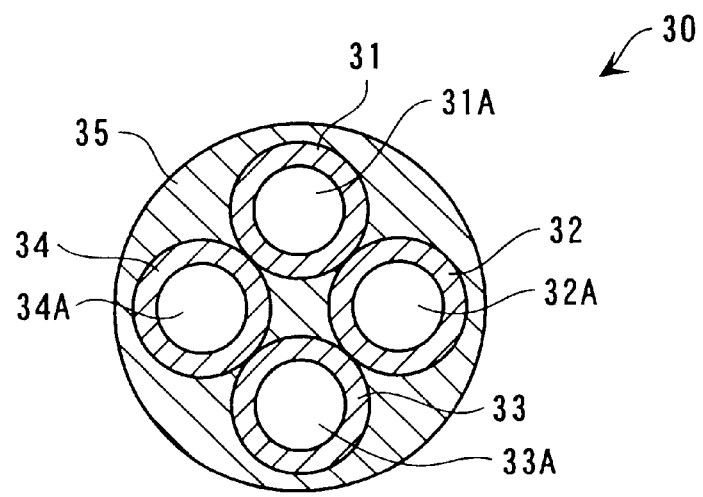
FIG. 5 is a cross-sectional view showing a cross-section of a tube of the apparatus of the aforesaid embodiment.

The tube used for the fluid delivering tube 30 is formed in a predetermined length and has thereinside a plurality of flow paths extending parallel along a longitudinal direction thereof. Specifically, as shown in FIG. 5, the tube includes a plurality of (four, in the present embodiment) thermoplastic-resin made tube elements 31, 32, 33 and 34 of a predetermined length respectively having flow paths 31A, 32A, 33A and 34A of different fluid passage rate. The tube elements 31, 32, 33 and 34 are bundled and outer surface thereof is unitedly covered with a covering member 35.

Respective tube elements 31 to 34 may be a single-layered tube, or alternatively, a covered tube considering reinforcement and handling. All of Polypropylene (PP), polyethylene (PE), polyacetals (POM), polycarbonate (PC), ABS, polyamide resin, and polystyrene (PS) can be used for a material of the tube element 31 to 34, however, transparent material is preferable. A flexible material is preferable for the covering member as a cover such as thermoplastic resin elastomer, polyolefin (LDPE, LLDEP) type elastomer, thermoplastic polyurethane elastomer, soft vinyl chloride resin and EVA.

The configuration of the cross-section of the tube element 31 to 34 is deformed unlike a circular opening of conventional flow rate control means. Some examples are shown in FIGS. 6(A) and 6(E).

Figure 6A:
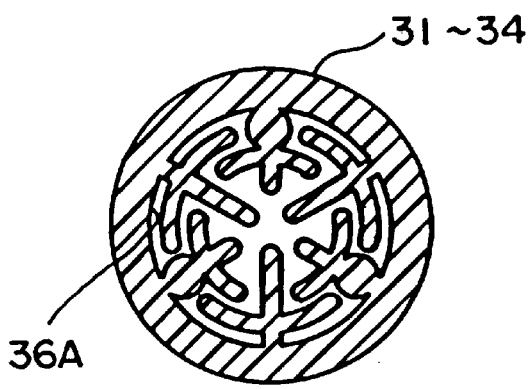
FIGS. 6(A) to 6(E) are cross-sectional views showing different configurations of cross-sections of tube elements of the apparatus of the aforesaid embodiment.

An opening 36A of the tube elements 31 to 34 shown in FIG. 6(A) has three branch-shaped projections of different two types alternatively projecting from an inner circumference of a circular base hole toward the center thereof.

Figure 6B:
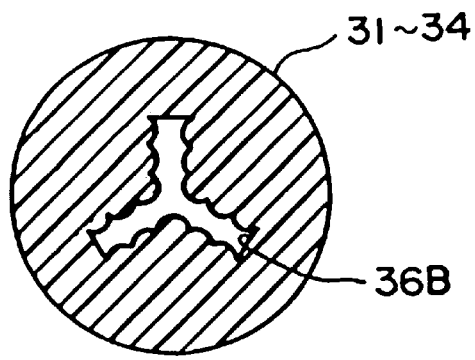

An opening 36B of the tube elements 31 to 34 shown in FIG. 6(B) has approximate rectangular-shaped groove extending in radial direction from the center of the tube elements 31 to 34 located by an even disposition of 120 degrees forming an approximate Y-shaped configuration, the groove having an inner side with concave and convex portion.

Figure 6C:
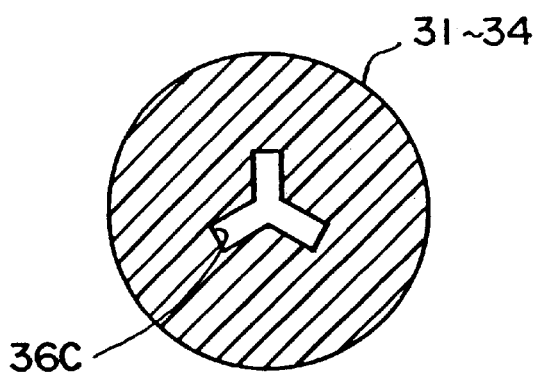

An opening 36C of the tube elements 31 to 34 shown in FIG. 6(C) has no concave and convex portion on the inner side unlike the opening 36B shown in FIG. 6(B) and the radial length of respective rectangular shape is shortened.

Figure 6D:
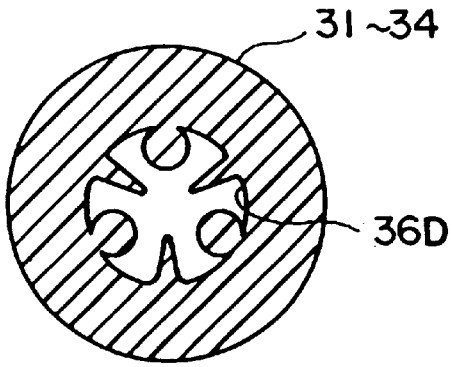
Figure 6E:
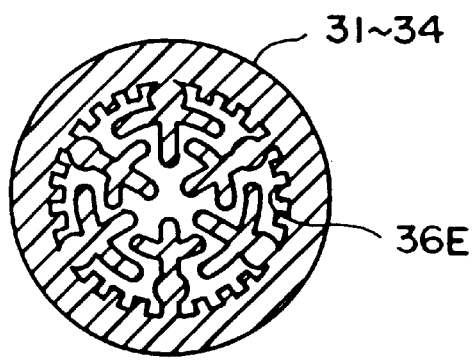

An opening 36D of the tube elements 31 to 34 shown in FIG. 6(D) has three thin triangle and circular projections alternatively projecting from an inner circumference of a circular base hole toward the center thereof.

An opening 36E of the tube elements 31 to 34 shown in FIG. 6(E) has branch-shaped projections with slightly deformed configuration of FIG. 6(A) and internal-gear-shaped concave and convex portion inside the base hole.

The deformation effect of deformed opening of the tube elements 31 to 34 is prominent when the deformation degree represented by square root of inner circumferential dimension of opening/opening cross-sectional area exceeds 7, and the above respective opening 36A to 36E have great deformation degree exceeding 7.

Incidentally, the above-described tube elements 31 to 34 having minute and deformed opening configuration can be molded using a die shown in Japanese Patent Application Laid-Open No. Sho 51-21927. In the molding method, a die for monofilament having a multiple of resin introduction hole provided to an area substantially the same as the outer diameter of the tube elements 31 to 34 and having no hole to a portion corresponding to the opening 36A to 36E is used. A molten resin monofilament is extruded from the introduction holes and the multiple of close monofilament is fused to obtain the tube elements 31 to 34 with minute and deformed configuration. However, the manufacturing method of the tube elements 31 to 34 is not limited to the method.

Figure 7:
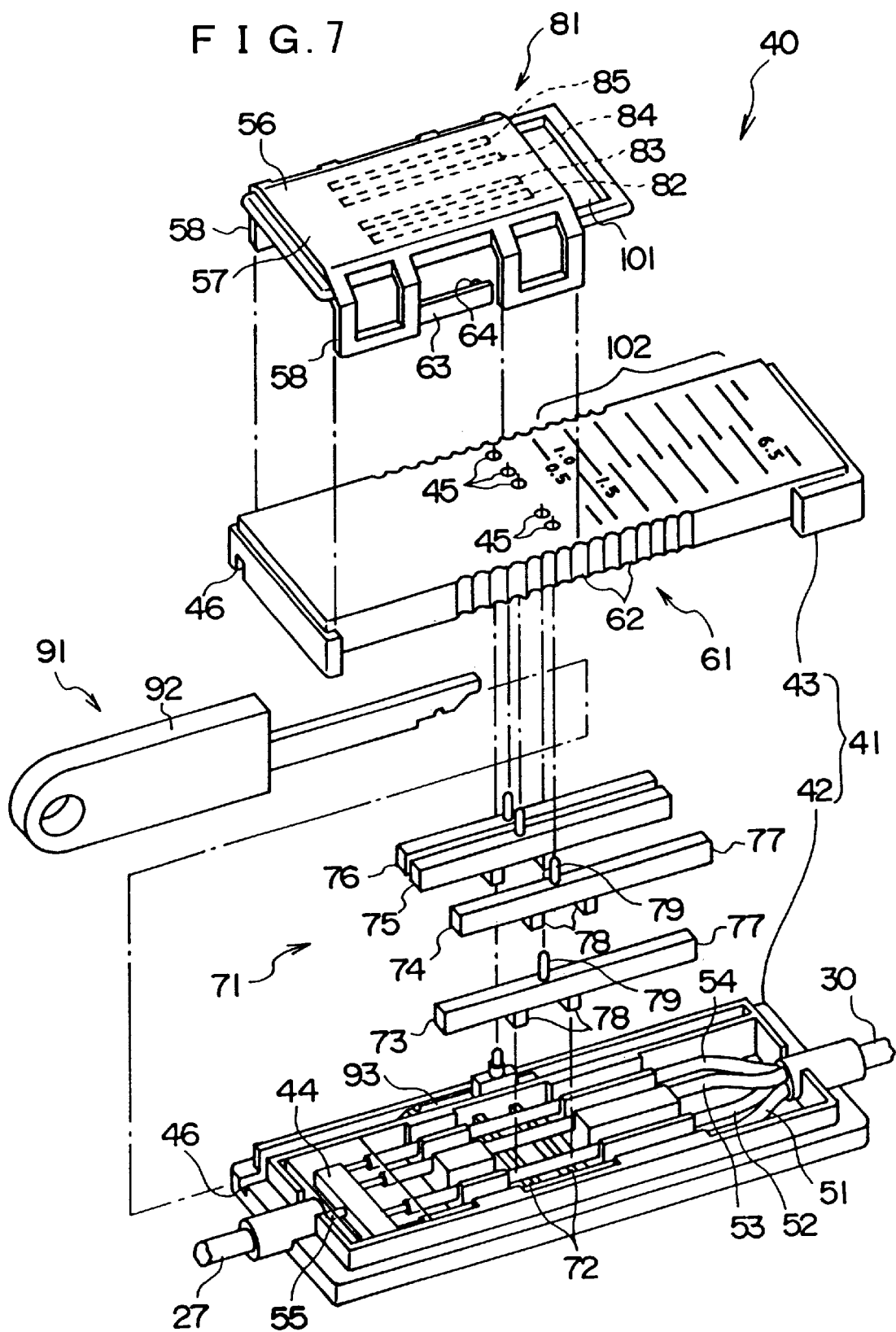
FIG. 7 is an exploded perspective view showing a flow control device used in the apparatus of the aforesaid embodiment.

As shown in FIG. 7, the flow control device 40 has a rectangular box-shaped body 41 composed of mutually engaging lower case 42 and upper case 43, a plurality of elastic flow control tube 51–54 provided in parallel in the body 51 and connected to respective tube elements 31–34, a single tube 55 connected to a distal end of the flow control tubes 51–54 through a communication portion 44 to be connected to the tube 27, a slider 56 as a slide member slidable relative to the body 41, a positioning mechanism 61 for locating the slider 56 by a predetermined pitch, a valve mechanism 71 for selectively pressing and shutting the flow control tubes 51 to 54 in accordance with the slide position of the slider 56 located by the positioning mechanism 61, and a lock mechanism 91 for locking the slide movement of the slider 56.

The slider 56 has a slide plate 57 and a frame-shaped holding piece 58 integrally provided on both sides of the slide plate 57 for slidably holding both sides of the body 41.

The positioning mechanism 61 includes a plurality of half-arcuate concave groove 62 formed on both sides of the body 41 (upper case 43) at a predetermined pitch interval, a plate spring 63 integrally provided to the holding piece 58 on both sides of the slider 56, and an engaging convex portion 64 provided at an end of the plate spring 63 for elastically engaging with the concave groove 62.

The valve mechanism 71 includes a stationary-side projection 72 provided to the body 41 for receiving the respective flow control tubes 51–54 and a plurality of press-piece 73–76 provided to the respective flow control tube 51–54 and being displaceable in a direction to press the flow control tube 51–54 toward the stationary-side projection 72, and a cam 81 provided to a backside of the slider 56 for selectively displacing the plurality of press-piece in accordance with the slide position of the slider 56 to selectively displace the plurality of press-piece 73–76 to press and shut the flow control tube 51–54.

The stationary projection 72 is provided at two locations longitudinally spaced along directions of the flow control tubes 51–54.

As shown in FIG. 8, the respective press-pieces 73–76 include a piece member 77, a movable-side projection 78 provided on a lower surface of the piece member 77 (opposite to the stationary-side projection 72 sandwiching the flow control tubes 51–54) and shifted relative to the stationary-side projection 72 in longitudinal direction of the flow control tube 51–54 (two locations shifted to the outside), and a pin 79 projecting from an upper surface of the piece member 77. The pin 79 projects from an upper surface of the body 41 through a hole 45 provided on the body 41 (the upper case 43).

Figure 9:
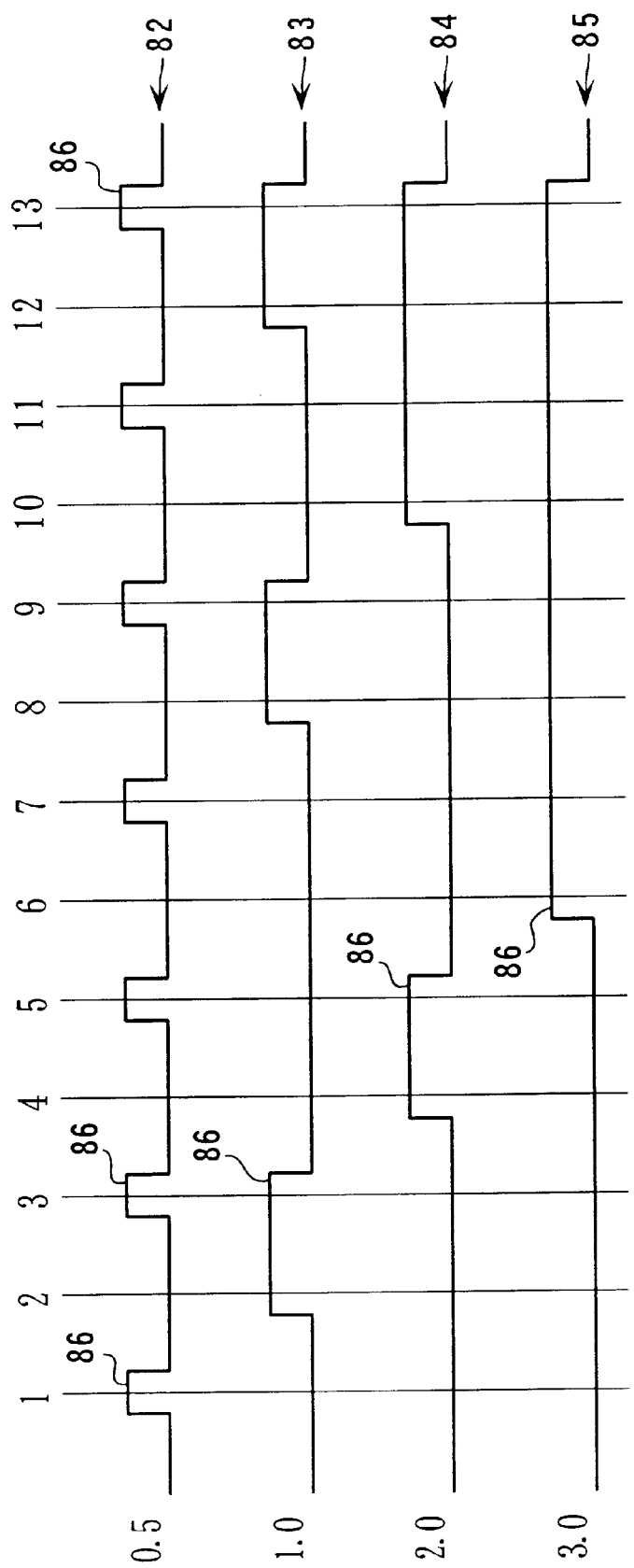
FIG. 9 is a view illustrating a cam groove of a flow control device used in the apparatus of the aforesaid embodiment.

The cam 81 includes four cam grooves 82–85 on a backside of the slider 56 and on a position corresponding to the pin 79 of the respective press-piece 73–76 along a slide direction of the slider 56. As shown in FIG. 9, the respective cam grooves 82–85 optionally include a groove 86 for maintaining the pin 79 of the respective press-piece 73–76 being projected from an upper surface of the body 41 at respective positioning locations (1)–(13) where the slider 56 is positioned by the positioning mechanism 61.

For instance, when the slider 56 is positioned at the positioning location (1), the groove 86 is formed only on the cam groove 82 corresponding to the pin 79. At this time, when the fluid passage rate of the flow control tubes 51–54 is 0.5 ml/hr, 1.0 ml/hr, 2.0 ml/hr, and 3.0 ml/hr respectively, the flow rate is 0.5 ml/hr. Further, when the slider 56 is positioned at the positioning location (2), the groove 86 is formed only on the cam groove 83 corresponding to the pin 79. In this case, the flow rate is 1.0 ml/hr. Further, when the slider 56 is positioned at the positioning location (3), the groove 86 is formed on the cam grooves 82 and 83 corresponding to the pin 79. In this case, the flow rate is 1.5 ml/hr.

When the slider 56 is located on the positioning locations (3) to (13) in a similar manner, the flow rate can be changed at 0.5 ml/hr interval, i.e. such as 2.0 ml/hr, 2.5 ml/hr, 3.0 ml/hr, 3.5 ml/hr, 4.0 ml/hr, 4.5 ml/hr, 5.0 ml/hr, 5.5 ml/hr, 6.0 ml/hr and 6.5 ml/hr.

As shown in FIGS. 10(A) and 10(B) in detail, the lock mechanism 91 includes a lock key 92 capable of being inserted and being drawn out of a key insert hole 46 of the body 41, a lock piece 93 accommodated in the body 41 and a plate-shaped biasing means 94 for constantly biasing the lock piece 93 upwardly. The lock piece 93 has a pin 95 protruding from an upper surface of the body 41 through the hole 45 opened on the body 41 (upper case 43) and for engaging a lock groove 97 formed on a backside of the slider 56 at a regular interval, and a press engaging portion 96 pressed downwardly by a distal end of the lock key 92 to be engaged when the lock key 92 is inserted into the body 41. Accordingly, when the lock key 92 is drawn out of the body 41, the lock key 92 locks a slide movement of the slider 56. And when the lock key 92 is inserted into the body 41, the lock key 92 allows the slide movement of the slider 56.

Figure 11:
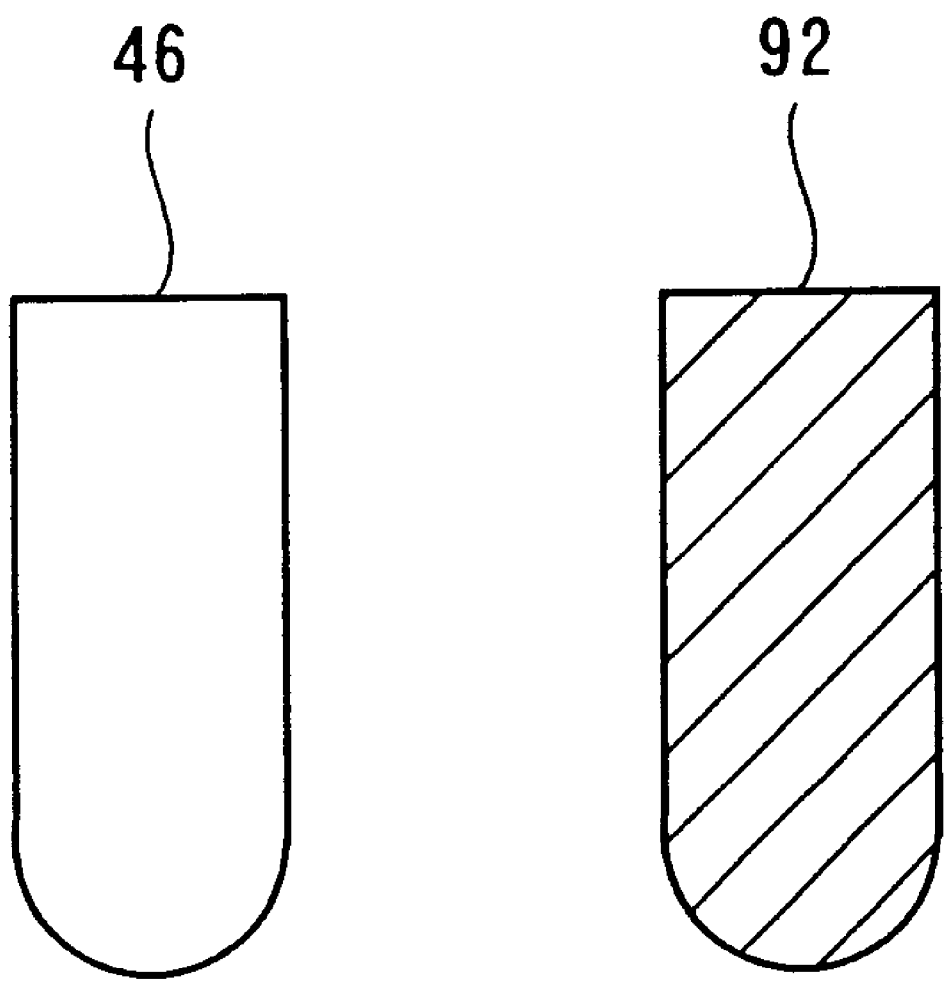
FIG. 11 is an illustration of cross-section of a key insert hole and a lock key of a flow control device used in the apparatus of the aforesaid embodiment.

Incidentally, a cross section of the key insert hole 46 and the lock key 92 is formed vertically asymmetrical, so that the lock key cannot be inserted to the key insert hole 46 when the lock key 92 is inversely inserted to the key insert hole 46. For instance, as shown in FIG. 11, the cross section of the key insert hole 46 and the lock key 92 is rectangular with a lower side thereof having concave arcuate shape.

The flow rate can be visibly recognized according to the slide position of the slider 56. More specifically, a window 101 as a flow rate indication index is provided to the slider 56 and a flow-rate display 102 for displaying the flow rate on a location corresponding to the window 101 at respective positioning location of the slider 56 located by the positioning mechanism 61 is provided on the body 41 (upper case 43).

A using method of the present embodiment will be described below.

Figure 12:
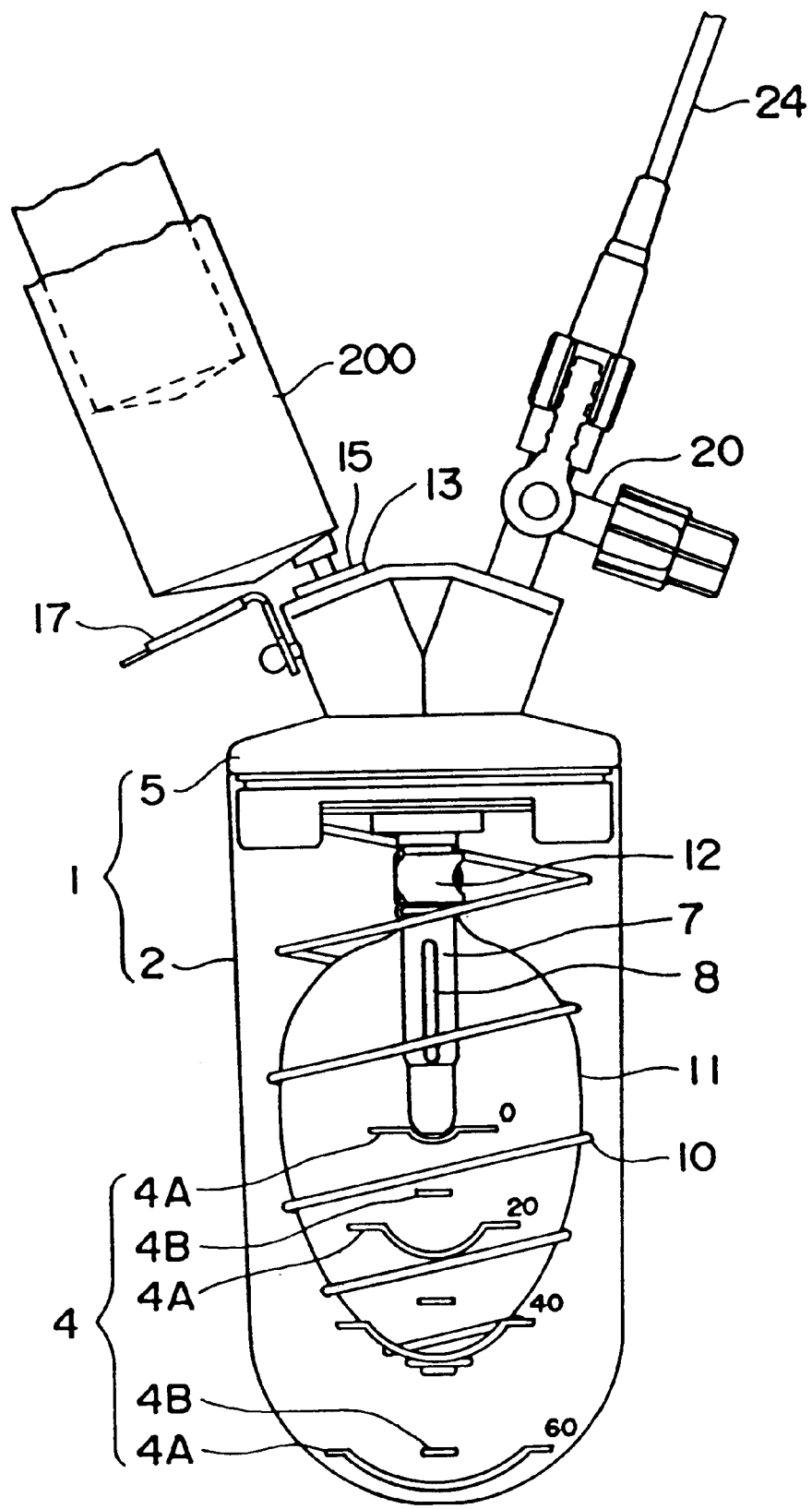
FIG. 12 is an illustration showing a condition when a liquid medicine is injected into the apparatus of the aforesaid embodiment.

When the liquid medicine is received in the rubber elastic film 11, the cap 17 is detached from the valve cylinder 15 of the check valve 13 and a pointed end of a syringe 200 in which the liquid medicine is contained is inserted in the valve cylinder 15 of the check valve 13 as shown in FIG. 12. When the liquid medicine inside the syringe 200 is pushed out at this state, the liquid medicine is received inside the rubber elastic film 11 through the check valve 13 to expand the rubber elastic film 11. The spring 10 is stretched in proportion to the expansion of the rubber elastic film 11, so that the amount of the liquid medicine received inside the rubber elastic film 11 can be read by the value of the scale 4 corresponding to the pointed end of the spring 10.

Figure 13:
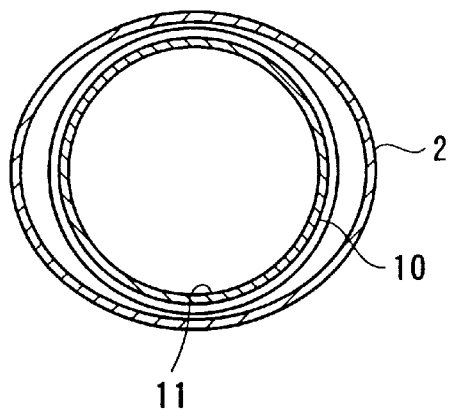
FIG. 13 is a cross-section showing relationship between the protection case and a rubber elastic film when the liquid medicine is injected into the apparatus of the aforesaid embodiment.

Subsequently, the rubber elastic film 11 abuts an inside of the cylinder body 2 of the protection case 1. Since the cross-section of the protection case 1 is formed in oval configuration as shown in FIG. 13, the contact area of the rubber elastic film 11 with the protection case 1 can be reduced as compared with circular configuration. Further, since the air is flow inside the protection case 1 can be ensured, the air inside the cylinder body 2 are discharged to the outside through the water-repellant breathable filter 9A in accordance with the expansion of the rubber elastic film 11. Accordingly, the liquid medicine can be accurately delivered little by little, and the attachment position of the air vent 9 is not restricted. After receiving the liquid medicine, the valve seat 14 of the check valve 13 is shut when the pointed end of the syringe 200 is pulled out from the check valve 13. Accordingly, the liquid medicine inside the rubber elastic film 11 does not leak to the outside.

Next, a syringe needle 29 is attached to the connector 28 at the distal end of the tube 27 and entered to human body. When the cock 23 of the three-direction valve 20 is opened, the liquid medicine is sequentially introduced to the human body through the fluid delivering tube 30, the flow control device 40 and the tube 27 at a small flow rate. Incidentally, the small flow rate of the present invention usually refers to around 0.8 ml/hr. However, the flow rate can be optionally determined in accordance with configuration of the deformed opening, length and viscosity of the liquid medicine and is not restricted to the above flow rate.

For changing the flow rate, the slider 56 of the flow control device 40 is slid.

For example, when the slider 56 is slid to the positioning location (1), the flow rate can be switched to 0.5 ml/hr. Further, when the slider 56 is slid to the positioning location (2), the flow rate is switched to 1.0 ml/hr. Further, when the slider 56 is slid to the positioning location (3), the flow rate is switched to 1.5 ml/hr.

When all the liquid medicine in the rubber elastic fluid 11 is injected into the human body changing the flow rate as necessary, the liquid medicine is filled in the rubber elastic film 11 similarly to the above description and the above-described operation is repeated. Incidentally, in order to remove air inside the rubber elastic film 11 before entering the syringe needle 29 to the human body, the protection case 1 is set upright with the lid body 5 upward and leave it while the cock 23 is made open.

According to the above-described embodiment, when the slider 56 is slid, the plurality of flow control tube 51–54 are selectively pressed and shut in accordance with slide position of the slider 56, so that the fluid flows through the flow control tube 51–54 that is not pressed and shut, thus controlling the flow rate by selecting the flow control tube 51–54 to be pressed and shut. Accordingly, for controlling the flow rate, the plurality of flow control tube 51–54 may be selectively pressed and shut, so that the process and arrangement can be simplified and the flow rate can be easily and accurately controlled.

Further, since the valve mechanism 71 includes the stationary-side projection 72, the plurality of press-piece 73–76 provided to the body 41 corresponding to the flow control tubes 51–54 displaceably in a direction for pressing the flow control tube 51–54 and having the movable-side projection 78 at the position shifted longitudinally along the flow control tubes 51–54 relative to the stationary-side projection 72, and a cam 81 for pressing and shutting the flow control tube 51–54 for selectively displacing the plurality of the press-piece 73–76 in accordance with the slide position of the slider 56 to press and shut the flow control tube 51–54, in other words, since the stationary-side projection 72 and the movable-side projection 78 are shifted longitudinally along the flow control tubes 51–54, when the press-pieces 73–76 are displaced by the cam 81 to press the flow control tubes 51–54, the flow control tubes 51–54 are sandwiched by the stationary-side projection 72 and the movable-side projection 78 to be shut in a sheared manner, so that the flow control tube 51–54 can be securely pressed and shut with smaller force as compared to an arrangement where the flow control tube is sandwiched between the stationary-side projection 72 and the movable-side projection 78 at mutually opposing position.

Further, since the press-pieces 73–76 press the flow control tubes 51–54 by the two movable-side projections spaced longitudinally along the flow control tubes 51–54, the press-pieces 73–76 can be displaced in parallel attitude without being tilted. Further, since the flow control tubes 51–54 are pressed and shut at the two locations, i.e. the flow control tubes 51–54 are pressed and shut by the two stationary-side projections 72 and the movable-side projection 78 spaced longitudinally along the flow control tubes 51–54, the flow control tubes 51–54 can be more securely pressed and shut selectively.

Since the positioning mechanism 61 for defining the position of the slider 56 for selectively pressing and shutting the flow control tube 51–54, in other words, since the slider 56 can be retained at the adjusted position, the adjusted flow rate can be stably continued.

Since the flow-rate-indicating window 101 is provided on the slider 56 and the flow-rate display for displaying the flow rate is provided at the position corresponding to the flow rate indicating window 101 on the respective positioning location of the slider 56 positioned by the positioning mechanism 61, the current flow rate can be recognized by reading the flow rate shown on the flow-rate display coincident with the flow-rate-indicating display 101, thus simplifying and facilitating adjustment thereof.

Further, after the lock key 92 is inserted to the body 41, whereat the slider 56 is slid to control the flow rate, the slide movement of the slider 56 is locked by drawing the lock key 92 off. Accordingly, for instance, when the present invention is applied to a liquid medicine injecting apparatus for continuously injecting minute amount of liquid medicine into human body, after the lock key 92 is inserted by a doctor or a nurse, whereby the flow rate is controlled by sliding the slider 56, the lock key 92 is drawn out to prevent flow rate control by the patient, so that security can be ensured.

Since the tube 30 having thereinside the elongated thermoplastic-resin tube elements 31 to 34 with deformed openings 36A to 36E is used in a flow rate control means instead of conventional short tube having circular opening, the flow rate can be controlled precisely by optionally setting the configuration of the opening and the tube length. When a conventional tube with circular opening is used as a conduit and a dust of a larger size than the inner diameter thereof is contained in the liquid medicine or the liquid medicine is likely to be coagulated, the liquid medicine flow tend to be entirely stopped because the opening is shut. On the other hand, since the tube 30 having predetermined tube elements 31 to 34 having deformed opening configuration is employed, the long side of the deformed opening 36A to 36E is not shut by dust. Accordingly, the blocking of the opening 36A to 36E can be more effectively prevented than the conventional tube having circular opening when the liquid medicine contains foreign substance such as dust and solid substance.

Though the tube with the conduit of the conventional tube having circular opening tends to be bent to shut by the weight of a lying patient, the tube elements 31 to 34 having deformed opening according to the present embodiment is tough against bend and is not likely to be shut even when the weight is applied. Therefore, the fluid delivering apparatus without shutting is safer and is significantly effective in a medical field where safety is of importance.

Furthermore, since the conduit function and the flow rate control function are both performed by the tube elements 31 to 34, the structure is simpler than the conventional combination of conduit tube and the flow rate control means.

When the conventional stainless thin tube and glass thin tube is used for performing both the conduit function and the flow rate control function, they are apt to be cracked, broken and difficult to be handled for being too thin. However, since the tube 30 made of thermoplastic resin is used in the present embodiment, deformed opening 36A to 36E having the predetermined configuration is easy to be manufactured, handled easily and both of the conduit function and the minute flow rate control function can be performed.

Incidentally, the scope of the present invention is not limited to the above embodiment and improvement and modification are also included within the scope of the present invention as long as an object of the present invention can be attained.

The number of the flow path formed inside the single fluid delivering tube 30 is not limited to four of the aforesaid embodiment, but more than one flow path may preferably be provided inside the tube 30.

Figure 14A:
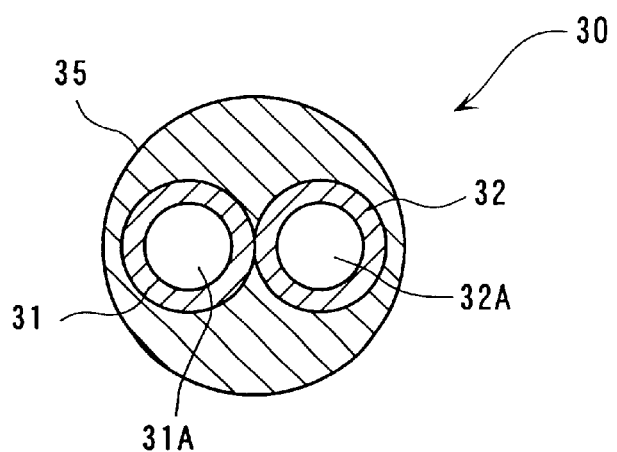
FIGS. 14(A) and (B) are cross-sections showing other examples of tubes used in the apparatus of the aforesaid embodiment.
Figure 14B:
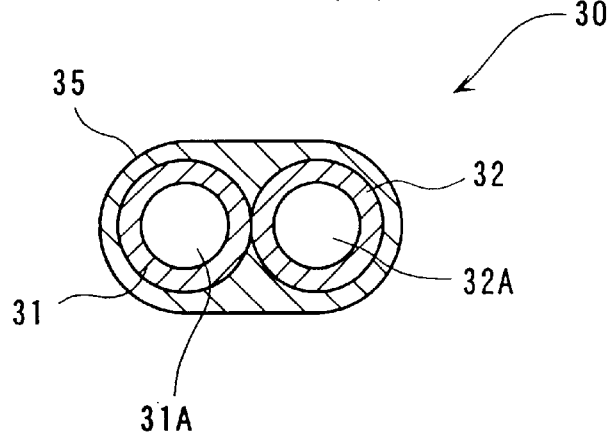

For instance, when two flow paths are provided, two tube elements 31 and 32 having flow paths 31A and 32A thereinside may be bundled and outside of the tube elements may be covered with the covering member 35 in a circular cross-section, as shown in FIG. 14(A). Alternatively, as shown in FIG. 14(B), two tube elements 31 and 32 having flow paths 31A and 32A thereinside may be bundled and outside of the tube elements may be covered with the covering member 35 in an ellipse cross-section. In the above arrangement, the fluid passage rate of the respective flow paths 31A and 32A may be the same or different with each other. Further, since either one of the flow paths 31A and 32A may be opened and closed in the flow path selecting means (flow rate switching device), the structure can be simplified.

In the aforesaid embodiment, the plurality of tube elements 31 to 34 is bundled and the outside thereof is unitedly covered by the covering member 35 to make a single tube. However, a thin core member may be set at a predetermined position in forming the tube and resin may be filled to the outside, so that the tube having thereinside a plurality of flow paths can be integrally formed after removing the core member.

Figure 15A:
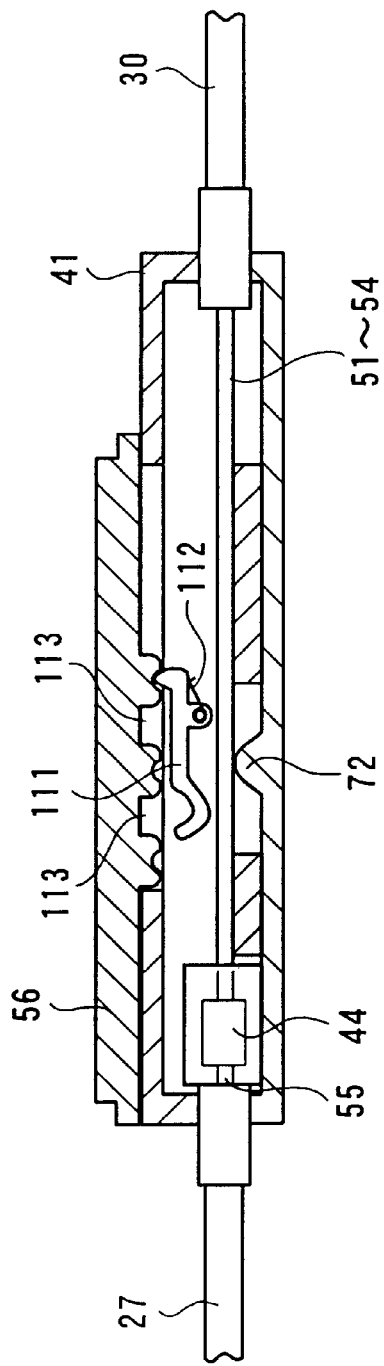
FIGS. 15(A) and (B) are cross-sections showing other examples of a valve mechanism used in the apparatus of the aforesaid embodiment.
Figure 15B:
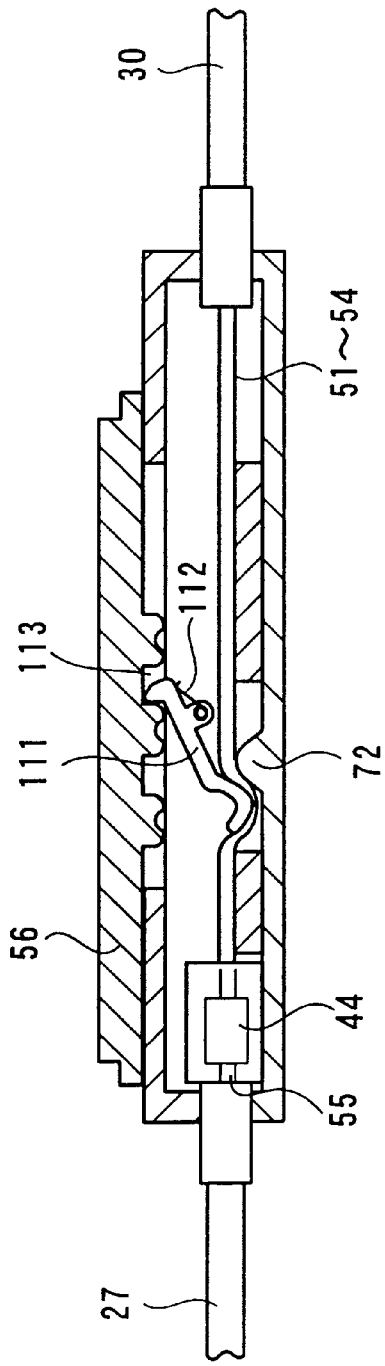

Further, the arrangement of the valve mechanism is not limited to the arrangement of the above-described embodiment, but other arrangement is possible. For instance, as shown in FIG. 15, a plurality of press lever 111 corresponding to respective flow control tubes 51–54 may be rotatably provided in the body 41, where a spring 112 for urging the press lever 111 in a direction for one end of the respective press lever 111 to press the flow control tubes 51–54 is provided, and a groove 113 may be optionally be provided on the lower surface of the slider 56, so that the one end of the press lever 111 presses the flow control tubes 51–54 when the groove 113 of the slider 56 is located on the other end of the press lever 111. Substantially the same effect as the above embodiment can also be obtained in this arrangement.

Though the slider 56 linearly and reciprocally slide relative to the body 41, the slider 56 may be rotated relative to the body and the flow control tubes 51–54 may be selectively pressed according to the predetermined angular position of the slider 56. In other words, the flow control tubes 51–54 may be provided on concentric circle in the body 41 and the valve mechanism 71 may be provided sandwiching the flow control tubes 51–54.

Further, though the fluid supply tube 30 having the tube elements 31–34 is connected to an upstream side of the flow control device 40 and a single tube 27 is connected to the downstream side, they may be connected in reverse. In other words, the single tube 27 may be connected to the upstream side of the flow control device 40 and the fluid supply tube having the tube elements 31–34 may be connected to the downstream side. The flow rate can also be controlled in the same manner in this arrangement.

The present invention can be applied to liquid medicine injecting apparatus for wide range of medical field such as injecting to veins and urinary organs, and application to obstetrics and gynecology. The present invention can also be used for injecting liquid medicine and nutrients to living body such as animals and fishes.

The present invention can also be used for gradually delivering water, (fluid) nutrients and liquid medicine (insecticide) to a plant. For instance, in order to gradually supply the water or the (fluid) nutrients in raising vegetables and flowers, it is only required that the distal end of the tube 30 or a needle attached to the distal end of the tube 30 is buried to the grounds around the vegetables and flowers. In the arrangement, the opening of the tube 30 is not shut even when the tube 30 is treaded on to bend the tube 30, thereby not interrupting the delivery of the fluid. When the liquid medicine is injected into trees, it is only required that the protection case 1 is hanged to the trees by an appropriate means and the needle at the distal end of the tube 30 is entered to the trees. In this case, the fluid is not limited to flow out downward from the hanged protection case 1 but the liquid medicine can be injected to an upper position of the protection case 1.

Further, the present invention can be applied for gradually delivering liquid medicines such as antibiotics, (fluid) bait and (fluid) nutrients for water grass to fish aquarium. In this case, the distal end of the tube 30 may be positioned in the aquarium without attaching the needle.

What is claimed is:

1. A flow control device, comprising:
 a body;
 a plurality of elastic flow control tubes provided inside the body, each of the flow control tubes having a supply end and a delivery end adapted to connect to a supply site and a delivery site, respectively, for transferring a fluid from the supply site to the delivery site in a controlled manner, at least one of the supply ends and the delivery ends of the flow control tubes being incorporated into a single fluid delivery tube;
 a slide member slidable relative to the body; and
 a valve mechanism for selectively pressing and shutting the flow control tubes in accordance with a slide position of the slide member.

2. The flow control device according to claim 1, wherein the valve mechanism includes a stationary-side projection provided to the body to receive the respective flow control tubes, a plurality of press-piece provided in the body correspondingly to the respective flow control tube and displaceable in a direction for pressing the flow control tube toward the stationary-side projection, the plurality of press-piece having a movable-side projection at a position opposite to the stationary-side projection sandwiching the flow control tube and shifted longitudinally along the flow control tube relative to the stationary-side projection, and a cam provided to the slide member for selectively displacing the plurality of press-piece in accordance with the slide position of the slide member to press and shut a corresponding flow control tube.

3. The flow control device according to claim 2, wherein the stationary-side projection is provided at two longitudinally spaced locations along the flow control tube, and
 wherein the movable-side projection is provided at two locations outside a position corresponding to the two stationary-side projections.

4. The flow control device according to claim 1, wherein a positioning mechanism for locating the slide member at a position for the slide member to selectively press and shut the flow control tube is provided between the body and the slide member.

5. The flow control device according to claim 4, wherein a flow rate indication index is provided on the slide member, and
 wherein a flow rate display is provided on the body for displaying a flow rate on a position corresponding to the flow rate indication index at respective positions of the slide member located by the positioning mechanism.

6. The flow control device according to claim 1, further comprising a lock mechanism including a lock key capable of inserting into and drawing off from the body, the lock key being drawn off from the body to lock a slide movement of the slide member, and the lock key being inserted to the body to allow the slide movement of the slide member.

7. The flow control device of claim 1, wherein the slide member is slidable along a delivery direction of the fluid being transferred in the flow control tubes.

8. The flow control device of claim 1, wherein the flow control tubes have different admissible flow rates.

9. A flow control device, comprising:
  a housing;
  a plurality of flexible flow control tubes located in the housing;
  a slide member mounted on and slidable relative to the housing; and
  a valve mechanism for selectively opening and shutting the flow control tubes in accordance with a plurality of slide positions of the slide member, the valve mechanism including
    at least one stationary side projection located in the housing below the flow control tubes; and
    a plurality of press pieces located in the housing each corresponding to and disposed above one of the flow control tubes, each of the press pieces having at least one movable side projection arranged along the respective flow control tube in a staggered manner with respect to the at least one stationary side projection, each of the press pieces being displaceable toward the respective flow control tube for pressing the respective flow control tube with the at least one movable side projection against the at least one stationary side projection, thereby shutting the respective flow control tube; and
    a cam provided on the slide member for selectively displacing the press pieces in accordance with the slide positions of the slide member to selectively open and shut the flow control tubes.

10. The flow control device of claim 9, wherein the at least one movable side projection is provided at two longitudinally spaced locations along the respective flow control tube, and the at least one stationary side projection is provided at another two longitudinally spaced locations between said two longitudinally spaced locations.

11. The flow control device of claim 9, further comprising a positioning mechanism provided between the housing and the slide member for positioning the slide member at the slide positions.

12. The flow control device of claim 9, further comprising a flow rate indicator provided on at least one of the slide member and the housing, for displaying a total flow rate of the flow control tubes in accordance with each of the slide positions of the slide member.

13. The flow control device of claim 9, further comprising a lock mechanism including a lock key removably insertable into the housing for locking the slide member to the housing to preclude a movement of the slide member among the slide positions when the lock key is inserted in the housing, and for unlocking the slide member from the housing to allow a movement of the slide member among the slide positions when the lock key is removed from the housing.

* * * * *